United States Patent
Chen

(10) Patent No.: US 7,251,307 B2
(45) Date of Patent: Jul. 31, 2007

(54) FAN-BEAM AND CONE-BEAM IMAGE RECONSTRUCTION USING FILTERED BACKPROJECTION OF DIFFERENTIATED PROJECTION DATA

(75) Inventor: Guang-Hong Chen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/284,500

(22) Filed: Nov. 22, 2005

(65) Prior Publication Data
US 2006/0109952 A1   May 25, 2006

Related U.S. Application Data

(60) Provisional application No. 60/630,930, filed on Nov. 24, 2004, provisional application No. 60/630,932, filed on Nov. 24, 2004.

(51) Int. Cl.
*H05G 1/60* (2006.01)
(52) U.S. Cl. .............................................. 378/4; 378/21
(58) Field of Classification Search .................. 378/4, 378/21, 901
See application file for complete search history.

(56) References Cited

U.S. PATENT DOCUMENTS

| | | | | |
|---|---|---|---|---|
| 4,555,760 A * | 11/1985 | Op de Beek et al. | .......... | 378/17 |
| 5,104,775 A | 4/1992 | Abe et al. | .................... | 430/372 |
| 5,257,183 A | 10/1993 | Tam | ............................... | 378/4 |
| 5,270,926 A | 12/1993 | Tam | ............................... | 378/4 |
| 5,400,255 A | 3/1995 | Hu | ................................. | 378/4 |
| 5,625,660 A | 4/1997 | Tuy | ............................. | 378/15 |
| 5,881,123 A * | 3/1999 | Tam | ............................... | 378/4 |
| 6,097,784 A | 8/2000 | Tuy | ............................... | 378/4 |
| 6,219,441 B1 | 4/2001 | Hu | ............................. | 382/131 |
| 6,415,013 B1* | 7/2002 | Hsieh et al. | ................... | 378/19 |
| 6,574,299 B1* | 6/2003 | Katsevich | ..................... | 378/15 |
| 2003/0081715 A1* | 5/2003 | Tam | ............................... | 378/4 |
| 2004/0258194 A1* | 12/2004 | Chen et al. | .................... | 378/4 |
| 2006/0067457 A1* | 3/2006 | Zamyatin et al. | ............... | 378/4 |

OTHER PUBLICATIONS

Yu et al. Feldkamp-type VOI reconstruction from super-short-scan cone-beam data Jun. 2004 Am. Assoc. Phys. Med. (6) p. 1358.*
Yu et al. Feldkamp-type VOI reconstruction from super-short-scan cone-beam data Jun. 2004 Am. Assoc. Phys. Med. (6) p. 1358.*
Tingliang Zhuang et al; Fan-beam and Cone-beam Image Reconstruction Via Filtering the Backprojection Image of Differentiated Projection Data; Phys.Med. Biol.
49 (2004) 5489-5503; Institute of Physics Publishing.

(Continued)

*Primary Examiner*—Courtney Thomas
*Assistant Examiner*—Alexander Taningco
(74) *Attorney, Agent, or Firm*—Quarles & Brady LLP

(57) ABSTRACT

A tomographic image reconstruction method produces either 2D or 3D images from fan beam or cone beam projection data by filtering the backprojection image of differentiated projection data. The reconstruction is mathematically exact if sufficient projection data is acquired. A cone beam embodiment and both a symmetric and asymmetric fan beam embodiment are described.

15 Claims, 7 Drawing Sheets

OTHER PUBLICATIONS

Yu Zou et al; Exact Image Reconstruction on PI-Lines From Minimum Data In Helical Cone-beam CT; Phys. Med. Biol. 49 (2004) 941-959; Institute of Physics Publishing.

Frederic Noo et al; A Two-Step Hilbert Transform Method For 2D Image Reconstruction; Phys. Med. Biol. 49 (2004) 3903-3923; Institute of Physics Publishing.

Zhuang, et al; Fan-Beam and Cone-Beam Image Reconstruction Via Filtering The Backprojection Image of Differentiated Projection Data; Phys. Med. Biol. 49 (2004) 5489-5503.

Zou, et al; Exact Image Reconstruction On PI-Lines From Minimum Data In Helical Cone-Beam CT; Phys. Med. Biol. 49 (2004) 941-959.

Noo, et al; A Two-Step Hilbert Transform Method for 2D Image Reconstruction; Phys. Med. Biol. 49 (2004) 3902-3923.

* cited by examiner

FAN-BEAM AND CONE-BEAM IMAGE RECONSTRUCTION USING FILTERED BACKPROJECTION OF DIFFERENTIATED PROJECTION DATA

CROSS-REFERENCE TO RELATED APPLICATIONS

This application is based on U.S. Provisional Patent Application Ser. No. 60/630,930, filed on Nov. 24, 2004 and entitled "FAN-BEAM AND CONE-BEAM IMAGE RECONSTRUCTION USING FILTERED BACK-PROJECTION OF DIFFERENTIATED PROJECTION DATA," and U.S. Provisional Patent Application Ser. No. 60/630,932, filed on Nov. 24, 2004 and entitled "FAN-BEAM IMAGE RECONSTRUCTION METHOD FOR TRUNCATED PROJECTION DATA."

STATEMENT REGARDING FEDERALLY SPONSORED RESEARCH

This invention was made with government support under Grant No. EB001683 awarded by the National Institute of Health. The United States Government has certain rights in this invention.

BACKGROUND OF THE INVENTION

The present invention relates to computed tomography (CT) imaging apparatus; and more particularly, to a method for reconstructing images from divergent beams of acquired image data.

In a current computed tomography system, an x-ray source projects a fan-shaped beam which is collimated to lie within an X-Y plane of a Cartesian coordinate system, termed the "imaging plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce the transmission profile.

The source and detector array in a conventional CT system are rotated on a gantry within the imaging plane and around the object so that the angle at which the x-ray beam intersects the object constantly changes. A group of x-ray attenuation measurements from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This process converts the attenuation measurements from a scan into integers called "CT numbers" or "Hounsfield units", which are used to control the brightness of a corresponding pixel on a display.

The term "generation" is used in CT to describe successively commercially available types of CT systems utilizing different modes of scanning motion and x-ray detection. More specifically, each generation is characterized by a particular geometry of scanning motion, scanning time, shape of the x-ray beam, and detector system.

As shown in FIG. 1, the first generation utilized a single pencil x-ray beam and a single scintillation crystal-photomultiplier tube detector for each tomographic slice. After a single linear motion or traversal of the x-ray tube and detector, during which time 160 separate x-ray attenuation or detector readings are typically taken, the x-ray tube and detector are rotated through 1° and another linear scan is performed to acquire another view. This is repeated typically to acquire 180 views.

A second generation of devices developed to shorten the scanning times by gathering data more quickly is shown in FIG. 2. In these units a modified fan beam in which anywhere from three to 52 individual collimated x-ray beams and an equal number of detectors are used. Individual beams resemble the single beam of a first generation scanner. However, a collection of from three to 52 of these beams contiguous to one another allows multiple adjacent cores of tissue to be examined simultaneously. The configuration of these contiguous cores of tissue resembles a fan, with the thickness of the fan material determined by the collimation of the beam and in turn determining the slice thickness. Because of the angular difference of each beam relative to the others, several different angular views through the body slice are being examined simultaneously. Superimposed on this is a linear translation or scan of the x-ray tube and detectors through the body slice. Thus, at the end of a single translational scan, during which time 160 readings may be made by each detector, the total number of readings obtained is equal to the number of detectors times 160. The increment of angular rotation between views can be significantly larger than with a first generation unit, up to as much as 36°. Thus, the number of distinct rotations of the scanning apparatus can be significantly reduced, with a coincidental reduction in scanning time. By gathering more data per translation, fewer translations are needed.

To obtain even faster scanning times it is necessary to eliminate the complex translational-rotational motion of the first two generations. As shown in FIG. 3, third generation scanners therefore use a much wider fan beam. In fact, the angle of the beam may be wide enough to encompass most or all of an entire patient section without the need for a linear translation of the x-ray tube and detectors. As in the first two generations, the detectors, now in the form of a large array, are rigidly aligned relative to the x-ray beam, and there are no translational motions at all. The tube and detector array are synchronously rotated about the patient through an angle of 180-360°. Thus, there is only one type of motion, allowing a much faster scanning time to be achieved. After one rotation, a single tomographic section is obtained.

Fourth generation scanners feature a wide fan beam similar to the third generation CT system as shown in FIG. 4. As before, the x-ray tube rotates through 360° without having to make any translational motion. However, unlike in the other scanners, the detectors are not aligned rigidly relative to the x-ray beam. In this system only the x-ray tube rotates. A large ring of detectors are fixed in an outer circle in the scanning plane. The necessity of rotating only the tube, but not the detectors, allows faster scan time.

Most of the commercially available CT systems employ image reconstruction methods based on the concepts of Radon space and the Radon transform. For the pencil beam case, the data is automatically acquired in Radon space. Therefore a Fourier transform can directly solve the image reconstruction problem by employing the well-known Fourier-slice theorem. Such an image reconstruction procedure is called filtered backprojection (FBP). The success of FBP reconstruction is due to the translational and rotational symmetry of the acquired projection data. In other words, in a parallel beam data acquisition, the projection data are invariant under a translation and/or a rotation about the object to be imaged. For the fan beam case, one can solve the image reconstruction problem in a similar fashion, however, to do this an additional "rebinning" step is required to transform the fan beam data into parallel beam data. The overwhelming acceptance of the concepts of Radon space and the Radon transform in the two dimensional case gives this approach to CT image reconstruction a paramount position in tomographic image reconstruction.

The Radon space and Radon transformation reconstruction methodology is more problematic when applied to three-dimensional image reconstruction. Three-dimensional CT, or volume CT, employs an x-ray source that projects a cone beam on a two-dimensional array of detector elements as shown in FIG. 5. Each view is thus a 2D array of x-ray attenuation measurements and a complete scan produced by acquiring multiple views as the x-ray source and detector array are revolved around the subject results in a 3D array of attenuation measurements. The reason for this difficulty is that the simple relation between the Radon transform and the x-ray projection transform for the 2D case in not valid in the 3D cone beam case. In the three-dimensional case, the Radon transform is defined as an integral over a plane, not an integral along a straight line. Consequently, we have difficulty generalizing the success of the Radon transform as applied to the 2D fan beam reconstruction to the 3D cone beam reconstruction. In other words, we have not managed to derive a shift-invariant FBP method by directly rebinning the measured cone beam data into Radon space. Numerous solutions to this problem have been proposed as exemplified in U.S. Pat. Nos. 5,270,926; 6,104,775; 5,257,183; 5,625,660; 6,097,784; 6,219,441; and 5,400,255.

It is well known that the projection-slice theorem (PST) plays an important role in the image reconstruction from two- and three-dimensional parallel-beam projections. The power of the PST lies in the fact that Fourier transform of a single view of parallel-beam projections is mapped into a single line (two-dimensional case) or a single slice (three-dimensional case) in the Fourier space via the PST. In other words, a complete Fourier space of the image object can be built up from the Fourier transforms of the sequentially measured parallel-beam projection data. Once all the Fourier information of the image object is known, an inverse Fourier transform can be performed to reconstruct the image. Along the direction of the parallel-beam projections, there is a shift-invariance of the image object in a single view of the parallel-beam projections. This is the fundamental reason for the one-to-one correspondence between the Fourier transform of parallel-beam projections and a straight line or a slice in the Fourier space. The name of the projection-slice theorem follows from this one-to-one correspondence.

In practice, divergent fan-beam and cone-beam scanning modes have the potential to allow fast data acquisition. But image reconstruction from divergent-beam projections poses a challenge. In particular, the PST is not directly applicable to the divergent-beam projections since the shift-invariance in a single view of projections is lost in the divergent-beam cases. One way to bypass this problem is to explicitly rebin the measured divergent-beam projections into parallel beam projections. This is the basic method currently used in solving the problem of fan-beam image reconstruction. After the rebinning process, one can take the advantages of the fast Fourier transforms (FFT) to efficiently reconstruct images. There are some issues on the potential loss of image spatial resolution due to the data rebinning.

But there are also some advantages in generating uniform distribution of image noise due to the non-local characteristic of the Fourier transform. Alternatively, a fan-beam projection can also be relabeled in terms of Radon variables so that the two-dimensional inverse Radon transform can be used to reconstruct images. In this way, a convolution-based fan-beam image reconstruction algorithm can be readily developed. The advantage of this type of reconstruction algorithm is the explicit filtered backprojection (FBP) structure. The disadvantage of the convolution-based method is that the weight in the backprojection step depends on the individual image pixels and thus noise distribution may not be uniform. This may pose problems in the clinical interpretation of tomographic images. In practice, different CT manufactures may utilize different strategies in balancing these advantages and disadvantages.

In the cone-beam case, it is much more complicated to rebin cone-beam projections into parallel-beam projections. The huge cone-beam data set also poses a big challenge to the potential data storage during the rebinning process. The main stream of the developments in cone-beam reconstruction has been focused on the development of approximate or exact reconstruction methods. For circular-based source trajectories, methods disclosed by L. A. Feldkamp, L. C. Davis, and J. W. Kress, "Practical Cone Beam Algorithm," J. Opt. Soc. Am. A 1, 612-619(1984); G. Wang, T. H. Lin, P. Cheng, and D. M. Shinozaki, "A general cone-beam reconstruction algorithm," IEEE Trans. Med. Imaging 12, 486-496 (1993); generate acceptable image quality up to moderate cone angles (up to 10° or so). Exact reconstruction algorithms have also been proposed and further developed for both helical source trajectory and more general source trajectories. Most recently, a mathematically exact and shift-invariant FBP reconstruction formula was proposed for the helical/spiral source trajectory A. Katsevich, "Theoretically exact filtered backprojection-type inversion algorithm for spiral CT," SIAM (Soc. Ind. Appl. Math.) J. Appl. Math. 62, 2012-2026 (2002). Starting with either the original Tuy's framework or Grangeat's framework, upon an appropriate choice of weighting function over the redundant data, shift-invariant FBP reconstruction formula has been derived for a general source trajectory. Similar to the fan-beam FBP reconstruction algorithm the characteristic of the convolution-based cone-beam reconstruction algorithm is the voxel-dependent weighting factor in the backprojection step. This will cause non-uniform distribution of the image noise. Moreover, due to the local nature of the newly developed convolution-based cone-beam image reconstruction algorithms, different image voxels are reconstructed by using cone-beam projection data acquired at different pieces of the source trajectory. Namely, different image voxels are reconstructed by using the data acquired under different physical conditions. This will potentially lead to some data inconsistency in dynamic imaging. Finally, the current convolution-based image reconstruction algorithms are only valid for some discrete pitch values in the case of helical/spiral source trajectory. This feature limits their application in a helical/spiral cone-beam CT scanner.

SUMMARY OF THE INVENTION

The present invention is an image reconstruction method which can be generically defined as an integral of a product of two functions, $K(\vec{x},\vec{x}')$ and $Q(\vec{x},\vec{x}')$. The function $Q(\vec{x},\vec{x}')$ is a weighted backprojection operation on the differentiated projection data acquired during a scan. The function $K(\vec{x}, \vec{x}')$ is the Fourier transform of one of the weighting factors, $\omega_1(\vec{x}, \hat{k})$, of the factorized weighting function $\omega(\vec{x}, \hat{k}; t)$. An efficient reconstruction method results when the second weighting factor $\omega_2(\vec{x}, t)$ of the weighting function $(\vec{x}, \hat{k}; t)$ is chosen to be a piecewise constant, or in other words, a function consisting of several constant pieces. In this case, the filtering kernel $K(\vec{x}, \vec{x}')$ is reduced to a Hilbert kernel or a linear combination of Hilbert kernels along different filtering lines.

More specifically, the invention is a method for producing an image from a plurality of projection views of a subject acquired at different view angles which includes: differentiating the acquired projection views; producing image values along filter lines in image space by backprojecting differentiated projection views; and filtering image values along each filter line. The invention may be employed with many different imagining modalities that use either symmetric or asymmetric diverging beams and either 2D fan beams or 3D cone beams.

GENERAL DESCRIPTION OF THE INVENTION

Figure 1:
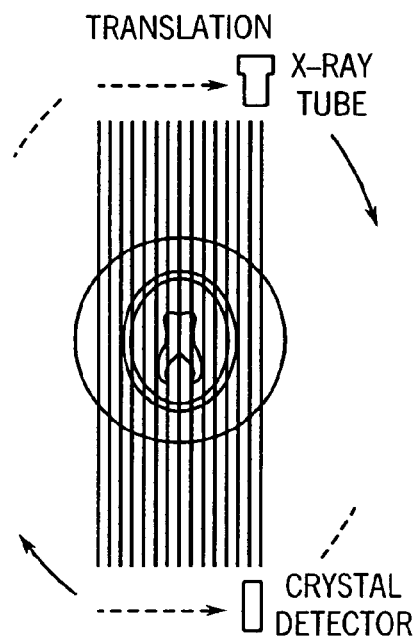
FIGS. 1-4 are schematic representations of different CT system geometries.
Figure 2:
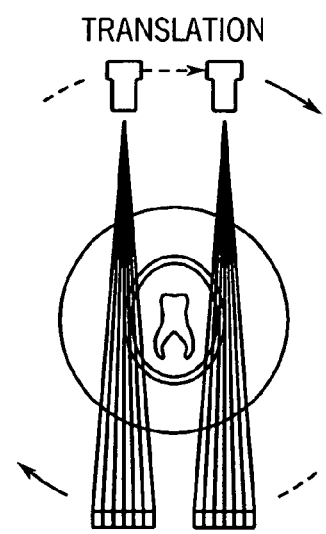
Figure 3:
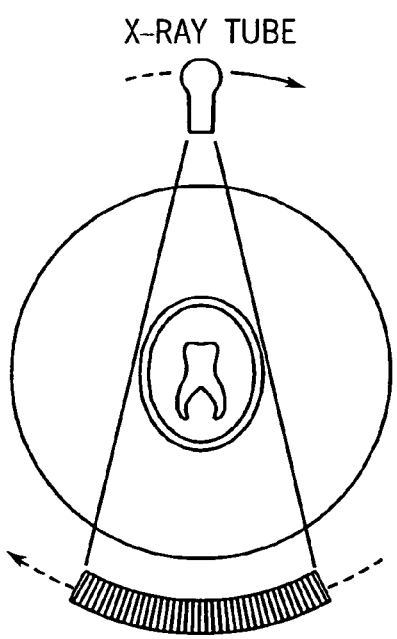
Figure 4:
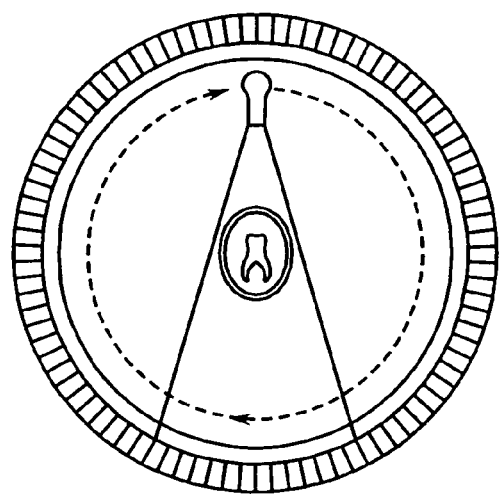

A compactly supported function $f(\vec{x})$ is the image function to be reconstructed. A general source trajectory is parameterized by a single parameter t, $t \in \Lambda = [t_i, t_f]$. Here $t_i$ and $t_f$ are assumed to be the view angles corresponding to the starting and ending points of an open source trajectory. A point on the source trajectory is measured in a laboratory system and denoted as $\vec{y}(t)$. The divergent fan-beam and cone-beam projections from a source point $\vec{y}(t)$ are defined as:

$$g[\vec{r}, \vec{y}(t)] = \int_0^{+\infty} ds f[\vec{y}(t) + s\vec{r}]. \tag{2.1}$$

An intermediate function $G_D[\vec{k}, \vec{y}(t)]$ is defined as the Fourier transform of the above divergent beam projections $g[\vec{r}, \vec{y}(t)]$ with respect to the variable $\vec{r}$, viz., $$G_D[\vec{k}, \vec{y}(t)] = \int_{R^D} d^D r g[\vec{r}, \vec{y}(t)] e^{i2\pi \vec{k} \cdot \vec{r}}. \tag{2.2}$$

The letter D labels the dimensions of a Euclidean space. Thus, D=2 corresponds to the fan-beam case, and D=3 corresponds to the cone-beam case.

The convention of decomposing a vector into its magnitude and a unit direction vector will be used, i.e. $\vec{r} = r\hat{r}$ and $\vec{k} = k\hat{k}$. Using the above two definitions, the following properties of the projections and intermediate functions can be readily demonstrated:

$$g[\hat{r}, \vec{y}(t)] = \frac{1}{r} \bar{g}[\hat{r}, \vec{y}(t)], \tag{2.3}$$

$$G_D[\vec{k}, \vec{y}(t)] = \frac{1}{k^{D-1}} \overline{G}_D[\hat{k}, \vec{y}(t)], \tag{2.4}$$

$$\mathrm{Im} G_D[-\vec{k}, \vec{y}(t)] = -\mathrm{Im} G_D[\vec{k}, \vec{y}(t)], \tag{2.5}$$

where $\mathrm{Im} G_D[\vec{k}, \vec{y}(t)]$ is the imaginary part of the intermediate function $G_D[-\vec{k}, \vec{y}(t)]$. In addition, $\bar{g}[\hat{r}, \vec{y}(t)]$ and $\overline{G}_D[\hat{k}, \vec{y}(t)]$ are the angular components of the projection g $[\vec{r}, \vec{y}(t)]$ and the intermediate function $G_D[\vec{k}, \vec{y}(t)]$ respectively.

With the above definitions and mathematical convention in hand, the image function $f(\vec{x})$ may be reconstructed using the modified Tuy-like formula:

$$f(\vec{x}) = \int_{S_k^{D-1}} d\hat{k} \sum_j \frac{\omega(\vec{x}, \hat{k}; t_j)}{2\pi \hat{k} \cdot \vec{y}'(t_j)} \frac{\partial}{\partial q} \mathrm{Im} \overline{G}_D[\hat{k}, \vec{y}(q)] \bigg|_{q=t_j}. \tag{2.6}$$

Here $(\vec{x}, \hat{k}; t_j)$ is a weighting function used in order to take into account the multiple solutions of the following equation:

$$\hat{k} \cdot [\vec{x} - \vec{y}(t_j)] = 0 \tag{2.7}$$

In the cone-beam case, the unit vector $\hat{k}$ is the normal vector of a plane that contains the line connecting a given image point $(\vec{x})$, and a source point $(\vec{y}(t_j))$. While, in the fan-beam case the unit vector $\hat{k}$ is the normal vector to the line connecting a given image point $(\vec{x})$, and a source point $(\vec{y}(t_j))$. This equation dictates the well-known Tuy data sufficiency condition: Any plane (cone-beam case) or straight line (fan-beam case) that passes through the region of interest (ROI) should intersect the source trajectory at least once. In Eq. 2.6 and Eq. 2.7, $\vec{y}(t_j)$ labels the j-th intersection point between the plane containing the image point $(\vec{x})$ and the source trajectory $\vec{y}(t_j)$. The set which is the union of all these solutions is labeled as $T(\vec{x}, \hat{k})$, viz., $$t_j \in T(\vec{x}, \vec{k}) = \{t | \hat{k} \cdot [\vec{x} - \vec{y}(t)] = 0\}. \tag{2.8}$$

The weighting function $\omega(\vec{x}, \hat{k}; t)$ satisfies the following normalization condition:

$$\sum_{t_j \in (\vec{x}, \hat{k})} \omega(\vec{x}, \hat{k}; t_j) = 1. \tag{2.9}$$

In addition, using property (2.5) and the inversion formula (2.6), the weighting function possesses the following symmetry:

$$\omega(\vec{x}, -\hat{k}; t) = \omega(\vec{x}, \hat{k}; t) \tag{2.10}$$

In order to proceed, we use the following well-known formula $$\sum_{t_j} \frac{\delta(t - t_j)}{|\hat{k} \cdot \vec{y}'(t_j)|} = \delta\{\hat{k} \cdot [\vec{x} - \vec{y}(t)]\} \tag{2.11}$$

to turn the summation over $t_j$ into an integral over the continuous variable t in Eq. (2.6). Consequently, we obtain:

$$f(\vec{x}) = \tag{2.12}$$

$$\frac{1}{2\pi} \int_\Lambda dt \int_{S_k^{D-1}} d\hat{k} \omega(\vec{x}, \hat{k}; t) \mathrm{sgn}[\hat{k} \cdot \vec{y}'(t)] \frac{\partial}{\partial q} \mathrm{Im}\overline{G}_D[\hat{k}, \vec{y}(q)] \bigg|_{q=t}$$

$$\delta[\hat{k} \cdot (\vec{x} - \vec{y}(t))].$$

Starting with the above equation, one can derive a shift-invariant FBP reconstruction formula for the fan-beam and cone-beam projections respectively. However, in order to derive the desired FBPD formula, it is insightful to use the following integration representation of the delta function:

$$\delta[\hat{k} \cdot (\vec{x} - \vec{y}(t))] = \int_{-\infty}^{+\infty} dk e^{i 2\pi k \hat{k} \cdot (\vec{x} - \vec{y}(t))} \tag{2.13}$$

to rewrite Eq. (2.12) as follows $$f(\vec{x}) = \frac{1}{2\pi} \int_\Lambda dt \int_0^{+\infty} dk \tag{2.14}$$

$$\int_{S^{D-1}} d\hat{k} \omega(\vec{x}, \hat{k}; t) \mathrm{sgn}[\hat{k} \cdot \vec{y}'(t)] \frac{\partial}{\partial q} \mathrm{Im}\overline{G}_D[\hat{k}, \vec{y}(q)] \bigg|_{q=t}$$

$$e^{i 2\pi k \hat{k} \cdot [\vec{x} - \vec{y}(t)]} + \frac{1}{2\pi} \int_\Lambda dt \int_{-\infty}^0 dk \int_{S^{D-1}} d\hat{k} \omega(\vec{x}, \hat{k}; t) \mathrm{sgn}$$

$$[\hat{k} \cdot \vec{y}'(t)] \frac{\partial}{\partial q} \mathrm{Im}\overline{G}_D[\hat{k}, \vec{y}(q)] \bigg|_{q=t} e^{i 2\pi k \hat{k} \cdot [\vec{x} - \vec{y}(t)]}.$$

By changing the variables $k \to -k$ and $\hat{k} \to -\hat{k}$ in the second term and using Eqs. (2.10) and (2.5), we obtain:

$$f(\vec{x}) = \frac{1}{\pi} \int_\Lambda dt \int_0^{+\infty} dk \int_{S^{D-1}} d\hat{k} \omega(\vec{x}, \hat{k}; t) \tag{2.15}$$

$$\mathrm{sgn}[\hat{k} \cdot \vec{y}'(t)] \frac{\partial}{\partial q} \mathrm{Im}\overline{G}_D[\hat{k}, \vec{y}(q)] \bigg|_{q=t} e^{i 2\pi k \hat{k} \cdot [\vec{x} - \vec{y}(t)]}$$

In this equation, the dummy variable k takes only non-negative values. Thus, the unit vector $\hat{k}$ and the non-negative value k can be combined as a complete vector, i.e., $\vec{k} = k\hat{k}$. Multiplying and dividing the angular component $\mathrm{Im} G_D[\hat{k}, \vec{y}(t)]$ by a factor $k^{D-1}$ and using property (2.4), we obtain:

$$f(\vec{x}) = \frac{1}{\pi} \int_\Lambda dt \int_{R_k^D} d\vec{k} \omega(\vec{x}, \hat{k}; t) \mathrm{sgn}[\hat{k} \cdot \vec{y}'(t)] \frac{\partial}{\partial q} \mathrm{Im} G_D[\hat{k}, \vec{y}(q)] \bigg|_{q=t} \tag{2.16}$$

$$e^{i 2\pi k \hat{k} \cdot [\vec{x} - \vec{y}(t)]},$$

where we have used the volume element $d\vec{k} = dk k^{D-1} d\hat{k}$ in a D-dimensional Euclidean space.

In the following, we use the definition of the intermediate function $G_D[\vec{k}, \vec{y}(t)]$ to calculate the derivative with respect to the source parameter:

$$\frac{\partial}{\partial q} \mathrm{Im} G_D[\hat{k}, \vec{y}(q)] \bigg|_{q=t} = \mathrm{Im} \int_{R^D} d\vec{r} \frac{\partial}{\partial q} g[\vec{r}, \vec{y}(q)]_{q=t} e^{-i 2\pi \vec{k} \cdot \vec{r}} = \tag{2.17}$$

$$\int_{R^D} d\vec{r} \frac{\partial}{\partial q} g[\vec{r}, \vec{y}(q)]_{q=t} \mathrm{Im}\left[e^{i 2\pi \vec{k} \cdot \vec{r}}\right] =$$

$$\int_{R^D} d\vec{r} \frac{\partial}{\partial q} g[\vec{r}, \vec{y}(q)]_{q=t} \frac{1}{2i}\left(e^{-i 2\pi \vec{k} \cdot \vec{r}} - e^{-i 2\pi \vec{k} \cdot \vec{r}}\right) =$$

$$\frac{1}{2i} \int_{R^D} d\vec{r} \frac{\partial}{\partial q} \{g[\vec{r}, \vec{y}(q)] - g[-\vec{r}, \vec{y}(q)]\} \bigg|_{q=t} e^{-i 2\pi \vec{k} \cdot \vec{r}}.$$

Note that the variable $\vec{r}$ is defined in a local coordinate system, i.e., $$\vec{r} = \vec{x}' - \vec{y}(t), \tag{2.18}$$

where $\vec{x}'$ is a point in the backprojection image space. Therefore, for the fan-beam and cone-beam projections at a given source position $\vec{y}(t)$, the substitution of Eq. (2.18) into Eq. (2.17), and the application of property (2.3) yields:

$$\frac{\partial}{\partial q} \mathrm{Im} \overline{G}_D[\hat{k}, \vec{y}(q)] \bigg|_{q=t} = \tag{2.19}$$

$$\frac{1}{2i} \int_{R^D} d\vec{x}' \frac{1}{|\vec{x}' - \vec{y}(t)|} \frac{\partial}{\partial q} \overline{g}^A[\hat{\beta}_{\vec{x}'}, \vec{y}(q)] \bigg|_{q=t} e^{-i 2\pi \vec{k} \cdot [\vec{x}' - \vec{y}(t)]},$$

where the unit vector $\hat{\beta}_{\vec{x}'}$ is defined as:

$$\hat{\beta}_{\vec{x}'} = \frac{\vec{x}' - \vec{y}(t)}{|\vec{x}' - \vec{y}(t)|}. \quad (2.20)$$

The modified fan-beam and cone-beam data $\bar{g}^A[\hat{\beta}_{\vec{x}'}, \vec{y}(t)]$ is defined as:

$$\bar{g}^A[\hat{\beta}_{\vec{x}'}, \vec{y}(t)] = \bar{g}[\hat{\beta}_{\vec{x}'}, \vec{y}(t)] - \bar{g}[-\hat{\beta}_{\vec{x}'}, \vec{y}(t)]. \quad (2.21)$$

The meaning of $\bar{g}^A[\hat{\beta}_{\vec{x}'}, \vec{y}(t)]$ will be elaborated upon later. After Eq. (2.16) and switching the order of integrations, we obtain:

$$f(\vec{x}) = \frac{1}{2\pi i} \int_{R^D} d\vec{x}' \int_{R^D_{\vec{k}}} d\vec{k} e^{i2\pi \vec{k} \cdot (\vec{x} - \vec{x}')} \quad (2.22)$$

$$\int_\Lambda dt \frac{\omega(\vec{x}, \hat{k}; t) \operatorname{sgn}[\hat{k} \cdot \vec{y}'(t)]}{|\vec{x}' - \vec{y}(t)|} \frac{\partial}{\partial q} \bar{g}^A[\hat{\beta}_{\vec{x}'}, \vec{y}(q)]\bigg|_{q=t}.$$

In the above equation, the integration over the variables t and $\vec{k}$ are coupled to one another through the factor $\omega(\vec{x}, \hat{k}; t) \operatorname{sgn}[\hat{k} \cdot \vec{y}'(t)]$. A key observation is to impose the following constraint, i.e., a factorization property, on the choice of the weighting functions:

$$\omega(\vec{x}, \hat{k}; t) = \omega_1(\vec{x}, \hat{k}) \omega_2(\vec{x}, t) \operatorname{sgn}[\hat{k} \cdot \vec{y}'(t)]. \quad (2.23)$$

In other words, we require that the weighting function is factorable so that the integrations over the variables t and $\vec{k}$ can be decoupled. This factorized weighting function is an important aspect of the present invention. Under this factorization condition, the reconstruction formula (2.22) can be further simplified as:

$$f(\vec{x}) = \int_{R^D} d\vec{x}' K(\vec{x}, \vec{x}') Q(\vec{x}, \vec{x}') \quad (2.24)$$

where $$K(\vec{x}, \vec{x}') = \frac{1}{2\pi i} \int_{R^D_{\vec{k}}} d\vec{k} \, \omega_1(\vec{x}, \hat{k}) e^{i2\pi \vec{k} \cdot (\vec{x} - \vec{x}')}, \quad (2.25)$$

$$Q(\vec{x}, \vec{x}') = \int_\Lambda dt \frac{\omega_2(\vec{x}, t)}{|\vec{x}' - \vec{y}(t)|} \frac{\partial}{\partial q} \bar{g}^A[\hat{\beta}_{\vec{x}'}, \vec{y}(q)]\bigg|_{q=t}. \quad (2.26)$$

In Eq. (2.24), the image reconstruction consists of two major steps. In the first step, the fan-beam or cone-beam projections are weighted by a weighting function $\omega_2(\vec{x}, t)$, and then processed by backprojecting the differentiated projection data to obtain the function $Q(\vec{x}, \vec{x}')$. In the second step, the function $Q(\vec{x}, \vec{x}')$ is multiplied by a kernel function $K(\vec{x}, \vec{x}')$, and then integration is performed over the entire Euclidean space spanned by the variable $\vec{x}'$, to obtain the reconstructed image value at the point $\vec{x}$.

Figure 8A:
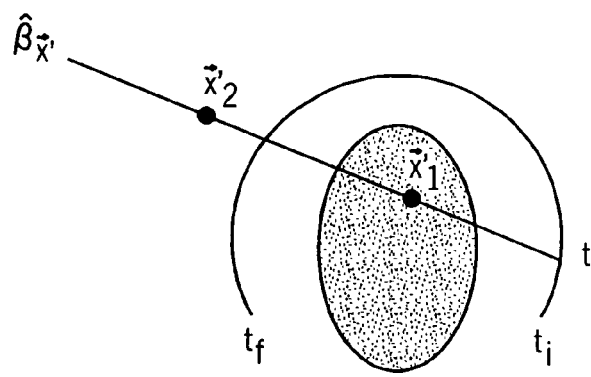
FIGS. 8a, 8b, 9, 10 and 11 are pictorial representations of the source trajectory and the field of view of the reconstructed image which are used to illustrate the underlying theory of the present invention.
Figure 8B:
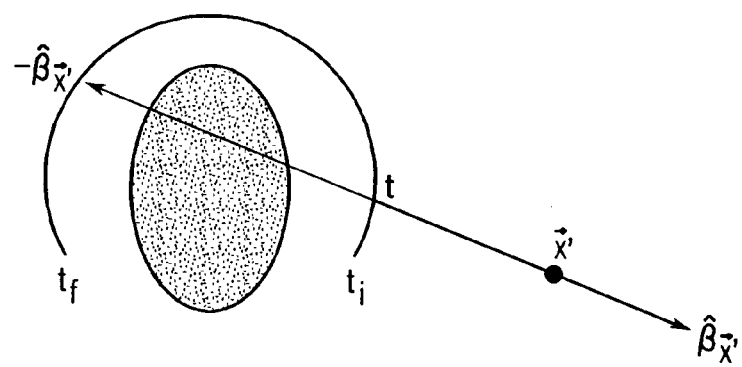

It is important to elaborate on the meaning of the modified fan-beam and cone-beam projections $\bar{g}^A[\hat{\beta}_{\vec{x}'}, \vec{y}(t)]$. As shown in FIG. 8, the modified projections $\bar{g}^A[\hat{\beta}_{\vec{x}'}, \vec{y}(t)]$ generally non-zero in the whole Euclidean space. Therefore, one potential problem in the derived image reconstruction method is that we have to numerically compute an integral over an infinite space. In addition, without an explicit choice of the weighting function, it is not yet clear whether the kernel function may posses an explicit and simple form. Therefore, up to this point, it is not certain whether Eq. (2.24)-Eq. (2.26) provide a computationally efficient and practical image reconstruction method. Although we require the weighting function to satisfy the factorization property (2.23), fortunately we still have sufficient degrees of freedom to choose an appropriate weighting function that will turn Eqs. (2.24)-(2.26) into a practical and efficient method. Namely, it is possible to obtain a one-dimensional filtering kernel. In this case, although the function $Q(\vec{x}, \vec{x}')$ is not band-limited along the filtering lines, one can still use the data from a finite range to reconstruct the image. In the following paragraphs, we will show how to choose the weighting function to make this kernel function simple and easy to implement in practice. Before we discuss specific examples of cone-beam and fan-beam image reconstruction via the FBPD, further clarification upon the properties of the weighting function is beneficial. Since the weighting function satisfies the normalization condition (2.9), the components $\omega_1(\vec{x}, \hat{k})$ and $\omega_2(\vec{x}, t)$ in Eq. (2.23) are not completely independent of one another. In fact, given a choice of the component $\omega_2(\vec{x}, t)$, the component $\omega_1(\vec{x}, \hat{k})$ is determined by the following equation:

$$\sum_{t_j \in T(\vec{x}, \hat{k})} \omega_1(\vec{x}, \hat{k}) \omega_2(\vec{x}, t_j) \operatorname{sgn}[\hat{k} \cdot \vec{y}'(t_j)] = 1. \quad (2.27)$$

Since the function $\omega_1(\vec{x}, \hat{k})$ does not depend on t, the summation over $t_j$ for the last two terms on left-hand-side of the above equation can be calculated by converting the summation into an integral:

$$\sum_{t_j \in T(\vec{x}, \hat{k})} \omega_2(\vec{x}, t_j) \operatorname{sgn}[\hat{k} \cdot \vec{y}'(t_j)] = \quad (2.28)$$

$$\int_\Lambda dt \omega_2(\vec{x}, t) \operatorname{sgn}[\hat{k} \cdot \vec{y}'(t)] |\hat{k} \cdot \vec{y}'(t)| \delta[\hat{k} \cdot (\vec{x} - \vec{y}(t))] =$$

$$\int_\Lambda dt \int_{-\infty}^{+\infty} dl \omega_2(\vec{x}, t) \hat{k} \cdot \vec{y}'(t) e^{i2\pi l \hat{k} \cdot [\vec{x} - \vec{y}(t)]} =$$

$$\frac{1}{2\pi i} \int_\Lambda dt \int_{-\infty}^{+\infty} \frac{dl}{l} \frac{\partial}{\partial t} e^{i2\pi l \hat{k} \cdot [\vec{x} - \vec{y}(t)]} \omega_2(\vec{x}, t) =$$

$$\int_\Lambda dt \omega_2(\vec{x}, t) \frac{\partial}{\partial t} h(\vec{x}, \hat{k}, t), \text{ where}$$

$$h(\vec{x}, \hat{k}, t) = \frac{1}{2\pi i} \int_{-\infty}^{+\infty} dl \frac{e^{i2\pi l \hat{k} \cdot [\vec{x} - \vec{y}(t)]}}{l} = \frac{1}{2} \operatorname{sgn}[\hat{k} \cdot (\vec{x} - \vec{y}(t))]. \quad (2.29)$$

The function $\omega_1(\vec{x},\hat{k})$ is the inverse of the above integral value in Eq. (2.28). Namely, the factor $\omega_1(\vec{x},\hat{k})$ is given by the following equation:

$$\omega_1^{-1}(\vec{x},\hat{k}) = \frac{1}{2}\int_\Lambda dt\,\omega_2(\vec{x},t)\frac{\partial}{\partial t}\text{sgn}\left[\hat{k}\cdot(\vec{x},\vec{y}(t))\right] \quad (2.30)$$

Therefore, for a given image point $\vec{x}$, as long as one piece-wise constant function $\omega_2(\vec{x},t)$ is chosen for a segment of sufficient source trajectory, the factor $\omega_1(\vec{x},\hat{k})$ is determined by the above equation. Consequently, the whole weighting function $\omega(\vec{x},\hat{k};t)$ is determined by equation (2.23). After the factors $\omega_1(\vec{x},\hat{k})$ and $\omega_1(\vec{x},t)$ are specified, an image reconstruction algorithm is given by equations (2.24)-(2.26).

We now develop an exact method for reconstructing an image from acquired cone beam data. For the conventional helical source trajectory with 1-pi data acquisition, there is one and only one pi-line for each point in the region-of-interest (ROI) defined by the cylindrical volume contained within the helix. However, in the case of an N-pi data acquisition scheme, there are multiple different lines that pass through each image point in the ROI and intersect the helical trajectory at two different points. Recently, the pi-line concept has also been generalized to the case of a helical trajectory with dynamical helical pitch and the case of a helical trajectory with a variable radius. For these generalized helical trajectories, under certain conditions, there is one and only one pi-line for each point in the ROI inside a helix. In addition, the pi-line concept has been generalized to the saddle trajectory. An important feature of the saddle trajectory is that the pi-lines are not unique for a point within the ROI. However, a common feature of the aforementioned trajectories is the existence of at least one pi-line or one generalized pi-line. The pi-line provides a natural geometric guideline in choosing the weighting function. If we denote the corresponding arc of a pi-line associated with an object point $\vec{x}$ as $I(\vec{x})=[t_{\pi_a}(\vec{x}), t_{\pi_b}(\vec{x})]$, we have a convenient choice for the component $\omega_2(\vec{x},t)$ in the weighting function:

$$\omega_2(\vec{x},t) = \begin{cases} 1, & \text{if } t \in I(\vec{x}), \\ 0, & \text{otherwise.} \end{cases} \quad (3.30)$$

With this choice of $\omega_2(\vec{x},t)$, the function $\omega_1(\vec{x},t)$ can be calculated as follows. Using Eq. (2.28), we have $$\sum_{t_j \in T(\vec{x},\hat{k})} \omega_2(\vec{x},t_j)\text{sgn}\left[\hat{k}\cdot\vec{y}'(t_j)\right] = \quad (3.31)$$

$$\int_{I(\vec{x})} dt\,\frac{\partial}{\partial t}h(\vec{x},\hat{k},t) = h(\vec{x},\hat{k},t_{\pi_a}) - h(\vec{x},\hat{k},t_{\pi_b}) =$$

$$\frac{1}{2}\{\text{sgn}[\hat{k}\cdot(\vec{x}-\vec{y}(t_{\pi_a}))] - \text{sgn}[\hat{k}\cdot(\vec{x}-\vec{y}(t_{\pi_b}))]\}.$$

Since $t_{\pi_a}$ and $t_{\pi_b}$ are the endpoints of the pi-line $I(\vec{x})$, we have $$\text{sgn}[\hat{k}\cdot(\vec{x}-\vec{y}(t_{\pi_a}))] - \text{sgn}[\hat{k}\cdot(\vec{x}-\vec{y}(t_{\pi_b}))] = 2\text{sgn}[\hat{k}\cdot(\vec{y}(t_{\pi_b})-\vec{y}(t_{\pi_a}))]. \quad (3.32)$$

Therefore, the function $\omega_1(\vec{x},\hat{k})$ can be determined using Eq. (2.27):

$$\omega_1(\vec{x},\hat{k}) = \text{sgn}[\hat{k}\cdot(\vec{y}(t_{\pi_b})-\vec{y}(t_{\pi_a}))]. \quad (3.33)$$

Using the explicit form of the component $\omega_1(\vec{x},\hat{k})$ in Eq. (3.33), the kernel function $K(\vec{x},\vec{x}')$ can be calculated from Eq. (2.25) as:

$$K(\vec{x},\vec{x}') = \frac{1}{2\pi i}\int_{R_{\hat{k}}^3} d\vec{k}\,\text{sgn}[\hat{k}\cdot\vec{e}_\pi(\vec{x})]e^{i2\pi\vec{k}\cdot(\vec{x}-\vec{x}')}, \quad (3.34)$$

where $\vec{e}_\pi(\vec{x})=\vec{y}(t_{\pi_b})-\vec{y}(t_{\pi_a})$ has been introduced along the pi-line, we obtain:

$$K(\vec{x},\vec{x}') = \frac{1}{2\pi^2}\frac{1}{z_\pi - z'_\pi}\delta(x_\pi - x'_\pi)\delta(y_\pi - y'_\pi), \quad (3.35)$$

where $\vec{x}$ and $\vec{x}'$ are now along pi-lines, viz. $\vec{x}=(x_\pi,y_\pi,z_\pi)$ and $\vec{x}'=(x'_\pi,y'_\pi,z'_\pi)$. Therefore, we obtain an explicit one-dimensional filtering kernel. Here we show that the same kernel can be used in any source trajectory provided that the concept of a pi-line is meaningful. Therefore, the filtering kernel is a shift-invariant Hilbert kernel along the pi-line. In fact, the same form of the function $\omega_2(\vec{x},t)$ as given in Eq. (3.30) may be chosen to reconstruct the points on an arbitrary straight line that passes one point and intersects the source trajectory at two different points $t_a$ and $t_b$. As long as the form of $\omega_2(\vec{x},t)$ is chosen as given in Eq. (3.30), the filtering kernel given in Eq. (3.34) is applicable.

The backprojection function $Q(\vec{x},\vec{x}')$ is given by:

$$Q(\vec{x},\vec{x}') = \int_{I(\vec{x})} dt\,\frac{1}{|\vec{x}'-\vec{y}(t)|}\frac{\partial}{\partial q}\bar{g}^A[\hat{\beta}_{\vec{x}'},\vec{y}(q)]\Big|_{q=t}. \quad (3.36)$$

The image point, $\vec{x}$, dependence of this function shows up through the pi-line. The function $\bar{g}^A[\hat{\beta}_{\vec{x}'},\vec{y}(t)]$ is defined in Eq. (2.21).

In summary, a mathematically exact image reconstruction method has been derived for any source trajectory provided that the concept of a pi-line or a generalized pi-line is meaningful and the source trajectory satisfies the Tuy data sufficiency condition. In this method, an image is reconstructed by filtering the backprojection image of differentiated projection data using a one-dimensional Hilbert kernel as given by Eq. (3.36) and Eq. (3.35).

Equation (3.30) gives one example of many possible selections of weighting functions. A specific choice of the weighting function $\omega_2(\vec{x},t)$ gives a specific image reconstruction formula. Namely, the filtering directions that are specified by the Fourier transforms of the factors $\omega_1(\vec{x},\hat{k})$ as indicated in equation (2.25) may be different. In the above example, the filtering direction is along a line that passes through the image point and intersects with the source trajectory at two different points (a pi-line or a generalized pi-line). The weighting factor $\omega_2(\vec{x},t)$ may also be chosen in such a way that the filtering direction is not along a pi-line. An example is given as below:

$$\omega_2(\vec{x},t) = \begin{cases} 1, & t \in [t_a, t_0] \\ -1, & t \in [t_0, t_b] \\ 0, & \text{otherwise} \end{cases} \quad (3.37)$$

where $t_0$ is any point on the source trajectory. Using this weighting factor $\omega_2(\vec{x},t)$, the weighting factor $\omega_1(\vec{x},\hat{k})$ is calculated as:

$$\omega_1(\vec{x},\hat{k}) = \operatorname{sgn}\left[\hat{k}\cdot\hat{e}(\vec{x},\vec{y}(t_0))\right], \quad \hat{e}(\vec{x},\vec{y}(t_0)) = \frac{\vec{x}-\vec{y}(t_0)}{|\vec{x}-\vec{y}(t_0)|} \quad (3.38)$$

If we align the z-axis of the vector $\vec{k}$ along the line labeled by the unit vector $$\hat{e}(\vec{x},\vec{y}(t_0)) = \frac{\vec{x}-\vec{y}(t_0)}{|\vec{x}-\vec{y}(t_0)|},$$

we obtain:

$$K(\vec{x},\vec{x}') = \frac{1}{2\pi^2}\frac{1}{z_e - z'_e}\delta(x_e - x'_e)\delta(y_e - y'_e) \quad (3.39)$$

where $\vec{x}$ and $\vec{x}'$ are now along pi-lines, $\vec{x}=(x_e,y_e,z_e)$ and $\vec{x}'=(x'_e,y'_e,z'_e)$ backprojection image is given by:

$$Q(\vec{x},\vec{x}') = \left(\int_{t_a}^{t_0} dt - \int_{t_0}^{t_b} dt\right) \frac{1}{|\vec{x}-\vec{y}(t)|}\frac{\partial}{\partial q}\bar{g}^A[\hat{\beta}'_{\vec{x}},(q)]\bigg|_{q=t} \quad (3.40)$$

Note that the filtering direction is along a straight line that connects image point $\vec{x}$ and pre-selected source point $\vec{y}(t_0)$. This filtering line only intersects the source trajectory at one point $\vec{y}(t_0)$. It is also important to note that the selection of point $\vec{y}(t_0)$ is arbitrary, therefore, we conclude that the filtering direction may be selected along any direction that passes through the image point $\vec{x}$.

In summary, using the factorized weighting function in Eq. (2.23) and a piece-wise constant weighting factor $\omega_2(\vec{x},t)$, an image reconstruction method may be developed using a one-dimensional Hilbert filtering of the backprojection image of differentiated projection data. This reconstruction method is applicable to any source trajectory that fulfills the Tuy data sufficiency condition and a pi-line or a generalized pi-line is meaningful. The filtering direction may be along any straight line that connects the image point and a preselected source point.

In this section, we consider image reconstruction from fan-beam projections on an arc source trajectory with radius r. The source trajectory is parameterized as:

$$\vec{y}(t) = r(\cos t, \sin t), t \in [t_i, t_f], \quad (4.37)$$

where $t_i$ and $t_f$ are view angles corresponding to the starting and ending points on the scanning path. For this scanning path, there are infinitely many lines that pass through an object point $\vec{x}$ and intersect the source trajectory at two points. In order to derive an explicit FBPD reconstruction method, we discuss two possible choices of the component $\omega_2(\vec{x},t)$ of the weighting function $\omega(\vec{x},\hat{k};t)$.

Case 1: Weighting function chosen for filtering along parallel lines

The intersection points of this horizontal line with the source trajectory are labeled by $\vec{y}(t_a(\vec{x}))$ and $\vec{y}(t_b(\vec{x}))$. The first choice of the function $\omega_2(\vec{x},t)$ is:

$$\omega_2(\vec{x},t) = \begin{cases} 1, & \text{if } t \in [t_a, t_b], \\ 0, & \text{otherwise.} \end{cases} \quad (4.38)$$

Using Eqs. (2.27) and (2.28), we obtain:

$$\omega_1(\vec{x},\hat{k}) = \operatorname{sgn}[\hat{k}\cdot(\vec{y}(t_b)-\vec{y}(t_a))]. \quad (4.39)$$

Substituting the above equation into Eq. (2.25), we obtain:

$$K(\vec{x},\vec{x}') = -\frac{1}{2\pi^2}\frac{1}{x-x'}\delta(y-y'). \quad (4.40)$$

Figure 10:
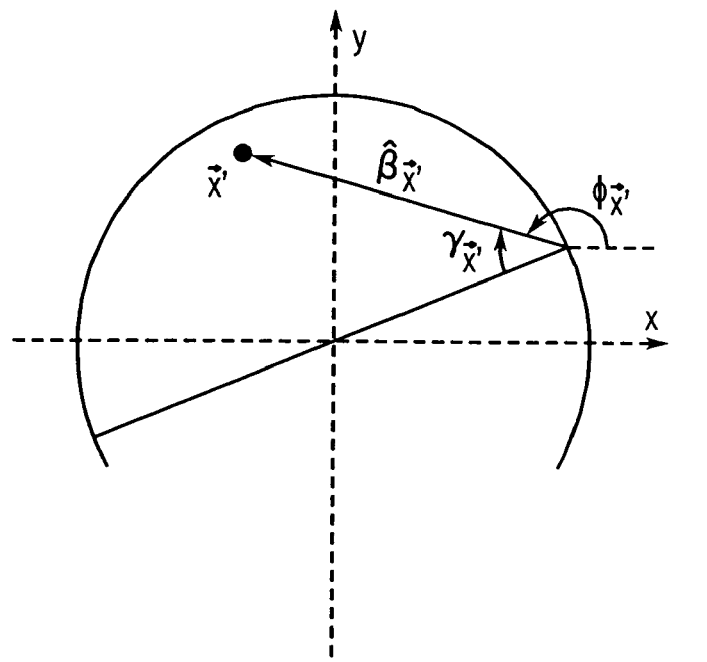

Here we have aligned the vector $\vec{k}$ along the horizontal x-direction. Thus, the filtering is a Hilbert transform conducted along the horizontal direction. In the case of an equi-angular detector, the derivative filtering backprojection function $Q(\vec{x},\vec{x}')$ is given by:

$$\begin{aligned}Q(\vec{x},\vec{x}') &= \int_{t_a(\vec{x}')}^{t_b(\vec{x}')} dt \frac{1}{|\vec{x}'-\vec{y}(t)|}\frac{\partial}{\partial q}\bar{g}^A[\hat{\beta}_{\vec{x}'},\vec{y}(q)]\bigg|_{q=t}, \\ &= \int_{t_a(\vec{x}')}^{t_b(\vec{x}')} dt \frac{1}{|\vec{x}'-\vec{y}(t)|}\left(\frac{\partial}{\partial t}-\frac{\partial}{\partial \gamma}\right) \\ &\quad \left[gm(\gamma,t)|_{\gamma=\gamma_{\vec{x}'}} - gm(\gamma,t)|_{\gamma=\gamma_{\vec{x}'}+\pi}\right],\end{aligned} \quad (4.41)$$

where $g_m(\gamma,t)$ is the measured fan-beam projection data at view angle t and fan angle $\gamma$. The values of $\gamma_{\vec{x}'}$ and $\hat{\beta}_{\vec{x}'}$ are determined by:

$$\gamma_{\vec{x}'}=\phi_{\vec{x}'}-t+\pi, \hat{\beta}_{\vec{x}'}=(\cos\phi_{\vec{x}'},\sin\phi_{\vec{x}'}), \quad (4.42)$$

as demonstrated in FIG. 10.

The final reconstruction formula is given by:

$$f(\vec{x}) = -\frac{1}{2\pi^2} \int_{-\infty}^{+\infty} dx' \int_{-\infty}^{+\infty} dy \frac{1}{x-x'} \delta(y-y') Q(\vec{x}, \vec{x}'). \quad (4.43)$$

For a given reconstruction point $\vec{x} = (x,y)$, the backprojection function $Q(\vec{x}, \vec{x}')$ should be calculated over an infinite horizontal line which passes through $\vec{x}$. Namely, $\vec{x}' = (x', y')$ in Eq. (4.41) extends along an infinite one-dimensional line. If the image function is compactly supported, a modified Hilbert transform may be used to perform the filtering process which only requires data over a finite range.

The implementation steps are summarized below:

Calculate the backprojection image values of differentiated fan-beam data on a Cartesian grid.

Figure 9:
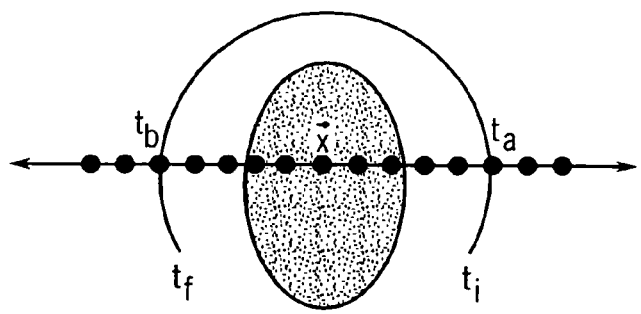

Filter the backprojection image with the Hilbert kernel along horizontal lines as shown in FIG. 9.

The advantage of this method is that the image reconstruction can be conducted directly on a Cartesian grid. However, the disadvantage is that, for different filtering lines, varying amounts of the projection data are used in the derivative backprojection step. Therefore, this choice of weighting function potentially leads to nonuniform noise distribution.

Case 2: Weighting function chosen for filtering along intersecting lines

Figure 11:
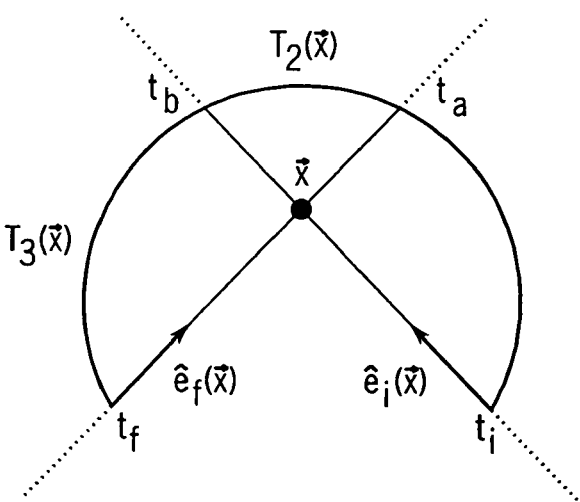

In this case, the objective is to use the same amount of projection data to reconstruct all the points within an ROI. For a given image point $\vec{x}$, two lines are used to connect the image point $\vec{x}$ with the two ending points at the view angles $t_i$ and $t_f$. As shown in FIG. 11 these two straight lines intersect with the scanning path at the view angles $t_a(\vec{x})$ and $t_b(\vec{x})$ respectively. Consequently, the scanning path is divided into three arcs:

$$T_1(\vec{x}) = \{t | t_i < t < t_a(\vec{x})\},$$

$$T_2(\vec{x}) = \{t | t_a(\vec{x}) < t < t_b(\vec{x})\},$$

$$T_3(\vec{x}) = \{t | t_b < t < t_f\}. \quad (4.44)$$

The function $\omega_2(\vec{x}, t)$ is chosen to be:

$$\omega_2(\vec{x}, t) = \begin{cases} a, & \text{if } t \in T_1(\vec{x}), \\ 1, & \text{if } t \in T_2(\vec{x}), \\ b, & \text{if } t \in T_3(\vec{x}), \end{cases} \quad (4.45)$$

where constants a and be satisfy the condition:

$$a + b = 1, \; a \neq b. \quad (4.46)$$

Using the above function $\omega_2(\vec{x}, t)$, the integral in the Eq. (2.28) can be directly calculated to yield:

$$\sum_{t_j \in T(\vec{x}, \hat{k})} \omega_2(\vec{x}, t_j) \text{sgn}[\hat{k} \cdot \vec{y}'(t_j)] = \quad (4.47)$$

$$\int_\Lambda dt \omega_2(\vec{x}, t) \frac{\partial}{\partial t} h(\vec{x}, \hat{k}, t) = -a \, \text{sgn}[\hat{k} \cdot (\vec{y}(t_b) - \vec{y}(t_i))] +$$

$$b \, \text{sgn}[\hat{k} \cdot (\vec{y}(t_a) - \vec{y}(t_f))],$$

where in the last step, the fact that the point $\vec{x}$ lies at the intersection between the line passing through $(\vec{y}(t_i), \vec{y}(t_b))$ and the line passing through $(\vec{y}(t_f), \vec{y}(t_a))$ has been used.

The inverse of the above equation provides the factor $\omega_1(\vec{x}, \hat{k})$ in the weighting function. The result is:

$$\omega_1(\vec{x}, \hat{k}) = \quad (4.48)$$

$$\frac{1}{a-b} \text{sgn}[\hat{k} \cdot (\vec{y}(t_b) - \vec{y}(t_i))] + \frac{b}{b-a} \text{sgn}[\hat{k} \cdot (\vec{y}(t_a) - \vec{y}(t_f))].$$

For simplicity, we introduce the following notation:

$$\hat{e}_i(\vec{x}) = \frac{\vec{y}(t_b) - \vec{y}(t_i)}{|\vec{y}(t_b) - \vec{y}(t_i)|}, \; \hat{e}_f(\vec{x}) = \frac{\vec{y}(t_a) - \vec{y}(t_f)}{|\vec{y}(t_a) - \vec{y}(t_f)|}. \quad (4.49)$$

Substituting Eq. (4.48) into Eq. (2/25), we obtain, $$K(\vec{x}, \vec{x}') = \frac{1}{2\pi^2(b-a)} \left\{ \frac{a}{(\vec{x}-\vec{x}') \cdot \hat{e}_i} \delta\left[(\vec{x}-\vec{x}') \cdot \hat{e}_i^\perp\right] + \frac{b}{(\vec{x}-\vec{x}') \cdot \hat{e}_f} \delta\left[(\vec{x}-\vec{x}') \cdot \hat{e}_f^\perp\right] \right\}, \quad (4.50)$$

where $\{\hat{e}_i^\perp, \hat{e}_i\}$ and $\{\hat{e}_f^\perp, \hat{e}_f\}$ are two sets of orthonormal bases, $$\hat{e}_i^\perp \cdot \hat{e}_i = 0, \; \hat{e}_f^\perp \cdot \hat{e}_f = 0. \quad (4.51)$$

Therefore, the filtering kernel is still the Hilbert kernel. However, the filtering lines are along the two directions $\hat{e}_i$ and $\hat{e}_f$, respectively. In this case, the backprojection operation is given by:

$$Q(\vec{x}, \vec{x}') = \left[ a \int_{T_1(\vec{x})} + \int_{T_2(\vec{x})} + b \int_{T_3(\vec{x})} \right] dt \frac{1}{|\vec{x}' = \vec{y}(t)|} \quad (4.52)$$

$$\left( \frac{\partial}{\partial t} - \frac{\partial}{\partial \gamma} \right) \left[ g_m(\gamma, t) \big|_{\gamma = \gamma_{\vec{x}}'} - g_m(\gamma, t) \big|_{\gamma = \gamma_{\vec{x} + \vec{x}'}'} \right],$$

where $\gamma_{\vec{x}}'$ is determined by Eq. (4.42) and the weighting factors a and b satisfy Eq. (4.46).

The final reconstruction formula is given by:

$$f(\vec{x}) = -\frac{1}{2\pi^2(b-a)} \int_{-\infty}^{+\infty} dx' \quad (4.53)$$

$$\int_{-\infty}^{+\infty} dy \left\{ a \frac{\delta[(\vec{x}-\vec{x}')\cdot \hat{e}_i^+]}{(\vec{x}-\vec{x}')\cdot \hat{e}_i} + b \frac{\delta[(\vec{x}-\vec{x}')\cdot \hat{e}_f^+]}{(\vec{x}-\vec{x}')\cdot \hat{e}_f} \right\} Q(\vec{x}, \vec{x}').$$

For a given reconstruction point $\vec{x} = (x,y)$, the backprojection function $Q(\vec{x}, \vec{x}')$ should be calculated over two infinite lines which pass through $\vec{x}$. Namely, $\vec{x}' = (x',y')$ in Eq. (4.52) extends along two infinite one-dimensional lines, as shown in FIG. 11.

The implementation steps are summarized below:

Calculate the backprojection image values of differentiated fan-beam data on a Cartesian grid.

Filter the backprojection image with the Hilbert kernel along the lines labeled by $\hat{e}_i$ and $\hat{e}_f$ shown in FIG. 11.

Sum the weighted and filtered contributions from the two filtering lines.

The advantage of this method is that the same amount of projection data is used for all the reconstructed points within an ROI. However, the disadvantage is that, for a single point a filtering process has to be performed along two filtering lines.

The weighting factors in Eqs. (3.37) and (3.38) may also be utilized in the fan-beam case to develop fan-beam image reconstruction procedures. In this case, the filtering line is along the line connecting the image point $\vec{x}$ and a preselected source point $\vec{y}(t_0)$.

Any other selections of a piece-wise constant weighting factor $\omega_2(\vec{x},t)$ will give a one-dimensional filtering kernel and thus, a new image reconstruction procedure by following the above examples. Namely, from a given piece-wise constant weighting factor $\omega_2(\vec{x},t)$, we calculated the weighting factor $\omega_1(\vec{x},\hat{k})$ using equation (2.20) and the backprojection image using equation (2.26). The filtering kernel is calculated according to Eq. (2.25) using the calculated weighting factor $\omega_1(\vec{x},\hat{k})$.

The steps for numerical implementation of the above image reconstruction methods are as follows:

Step 1: For a given direction $\hat{\beta}_{\vec{x}'}$, calculate the differentiation of the projection data $\bar{g}^d[\hat{\beta}_{\vec{x}'}, \vec{y}(t)]$ with respect to the source parameter t.

Step 2: Calculate the backprojection image values $Q(\vec{x}, \vec{x}')$ for the points along the filtering direction using Equation (2.26).

Step 3: Numerically calculate the Hilbert transform of the backprojection image along the filtering line to obtain image values $f(\vec{x})$ using the following equation:

$$f(x_f, y_f, z_f) = \quad (4.54)$$

$$-\frac{1}{2\pi^2} \int_{-\infty}^{+\infty} dx'_f \frac{1}{x_f - x'_f} Q(x_f, y_f, z_f; x'_f, y'_f = y_f, z'_f = z_f)$$

where the subscript "f" means the Hilbert transform is one-dimensional and is along the filtering direction.

Note that the backprojection image of differentiated projection data is not compactly supported. Thus, a direct implementation of Hilbert filtering in Equation (4.54) will introduce numerical errors. Fortunately, for a compactly supported image object, it is known that samples in a finite range may be utilized to accurately reconstruct the object. Namely, the integral range in Equation (4.54) may be finite. To be more specific, the following modified formula can be utilized in a numerical implementation:

$$f(x_f, y_f, z_f) = \quad (4.55)$$

$$\frac{1}{2\pi^2 \sqrt{(B-x_f)(x_f-A)}} \left[ \int_A^B dx'_f \frac{\sqrt{(B-x'_f)(x'_f-A)}}{x_f - x'_f} Q(x_f, y_f, z_f; x'_f, y'_f = y_f, z'_f = z_f) + C \right]$$

Where the constants A and B are integral limits which should be selected outside of the image support. The constant C is given by the projection data along the filtering direction from the following relation:

$$C = -2\pi g_m(\hat{\beta}_f, t)| \quad (4.56)$$

where $\hat{\beta}_f$ is along the filtering direction.

When a flat-panel detector is utilized to detect the attenuated X-rays, the derivative may be calculated in terms of detector coordinates u, v, and source parameter t. Namely, the differentiated projection data is given by:

$$g_d(u, v, t) = \left( \frac{D^2 + u^2}{D} \frac{\partial}{\partial u} + \frac{uv}{D} \frac{\partial}{\partial v} - \frac{\partial}{\partial t} \right) g_m(u, v, t). \quad (4.57)$$

If a colinear detector is utilized to detect the attenuated x-rays in fan-beam case, then the index v is suppressed in equation (4.57).

When a curved CT-detector is utilized to detect the attenuated x-rays, the above derivative may also be calculated in terms of detector coordinates $\gamma$, $\alpha$, and source parameter t. Where parameter $\gamma$ is the parameter along the transverse direction (fan angle) and the parameter $\alpha$ is the cone angle.

$$g_d(\gamma, \alpha, t) = \left( \frac{\partial}{\partial \gamma} - \frac{\partial}{\partial t} \right) g_m(\gamma, \alpha, t) \quad (4.58)$$

If the detector row is one, this is just the conventional fan beam case. In this case, the cone angle index $\alpha$ is suppressed.

DESCRIPTION OF THE PREFERRED EMBODIMENT

Figure 6:
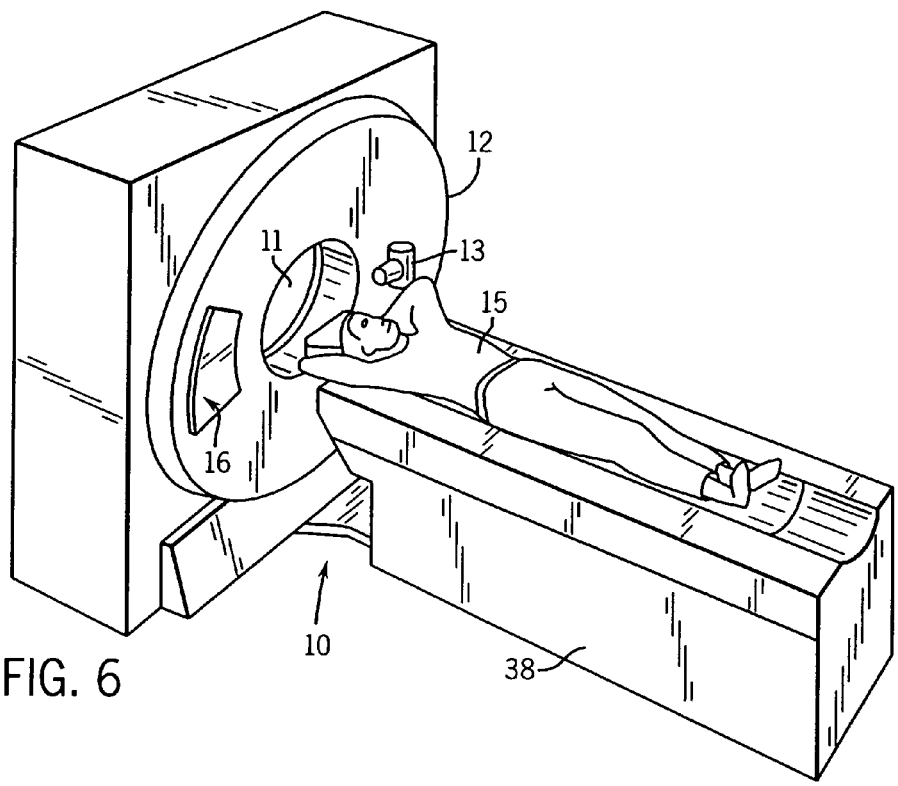
FIG. 6 is a pictorial view of a CT system which employs the present invention.
Figure 7:
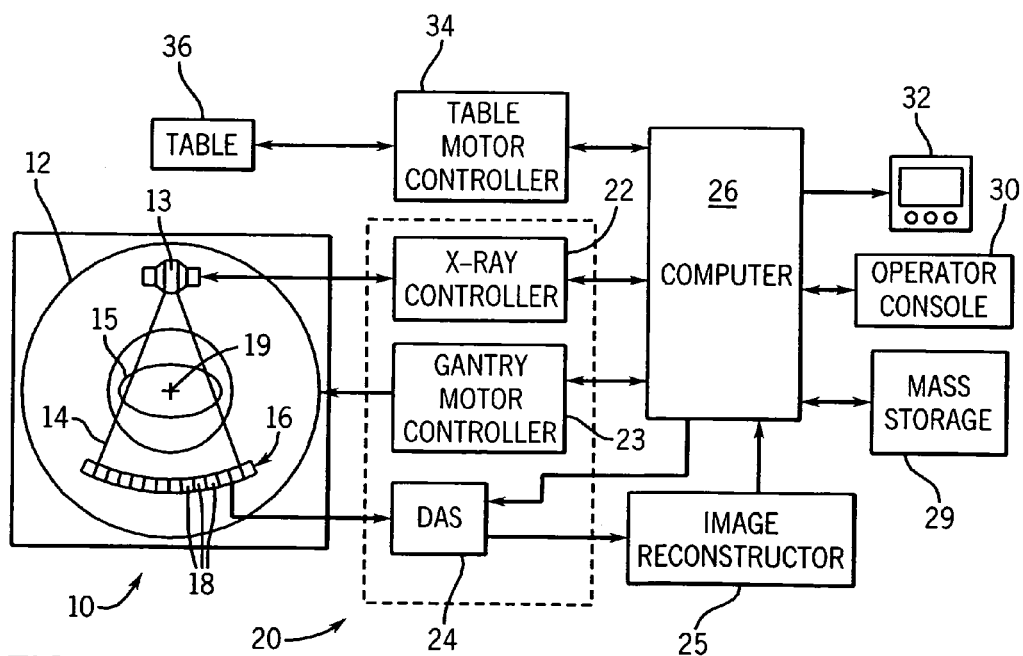
FIG. 7 is a block diagram of the CT system of FIG. 6.

With initial reference to FIGS. 6 and 7, a computed tomography (CT) imaging system 10 includes a gantry 12 representative of a "third generation" CT scanner. Gantry 12 has an x-ray source 13 that projects a cone beam of x-rays 14 toward a detector array 16 on the opposite side of the gantry. The detector array 16 is formed by a number of detector elements 18 which together sense the projected x-rays that pass through a medical patient 15. Each detector element 18 produces an electrical signal that represents the intensity of an impinging x-ray beam and hence the attenuation of the beam as it passes through the patient. During a scan to acquire x-ray projection data, the gantry 12 and the components mounted thereon rotate about a center of rotation 19 located within the patient 15.

The rotation of the gantry and the operation of the x-ray source 13 are governed by a control mechanism 20 of the CT system. The control mechanism 20 includes an x-ray controller 22 that provides power and timing signals to the x-ray source 13 and a gantry motor controller 23 that controls the rotational speed and position of the gantry 12. A data acquisition system (DAS) 24 in the control mechanism 20 samples analog data from detector elements 18 and converts the data to digital signals for subsequent processing. An image reconstructor 25, receives sampled and digitized x-ray data from the DAS 24 and performs high speed image reconstruction according to the method of the present invention. The reconstructed image is applied as an input to a computer 26 which stores the image in a mass storage device 29.

The computer 26 also receives commands and scanning parameters from an operator via console 30 that has a keyboard. An associated cathode ray tube display 32 allows the operator to observe the reconstructed image and other data from the computer 26. The operator supplied commands and parameters are used by the computer 26 to provide control signals and information to the DAS 24, the x-ray controller 22 and the gantry motor controller 23. In addition, computer 26 operates a table motor controller 34 which controls a motorized table 36 to position the patient 15 in the gantry 12.

Figure 5:
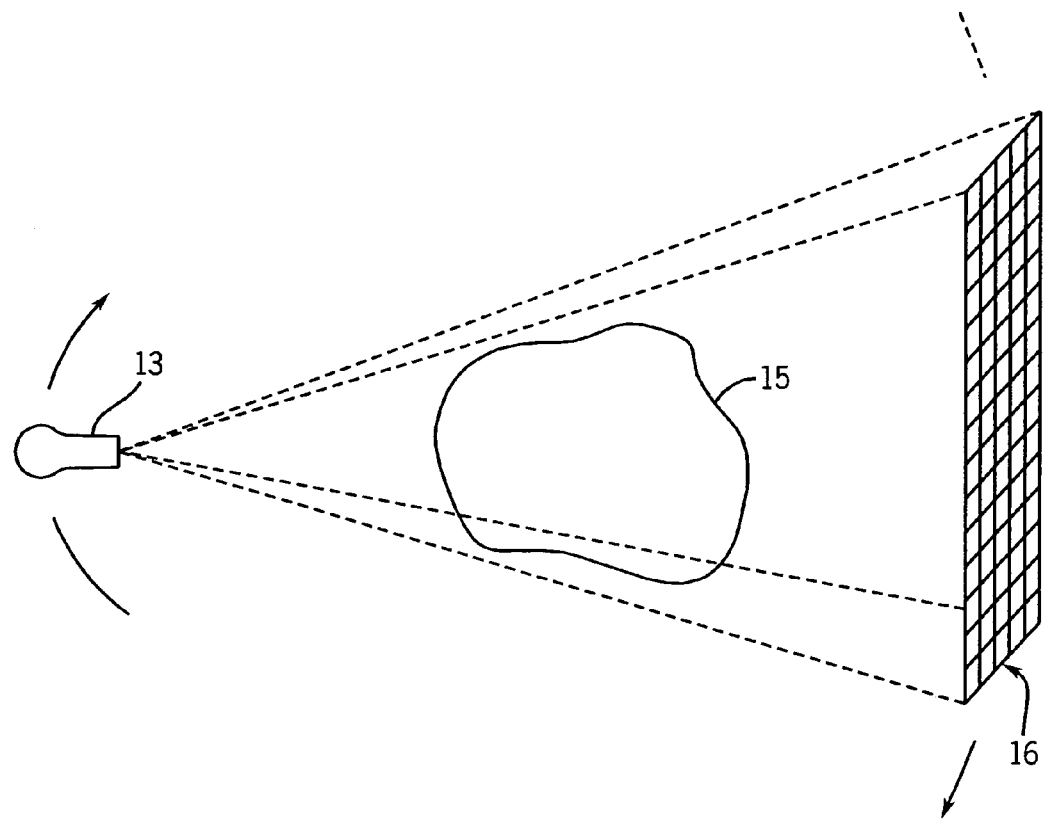
FIG. 5 is a pictorial representation of a 3D, or volume, CT system.

As shown best in FIG. 5, in a preferred embodiment of the present invention the detector array 16 is a flat array of detector elements 18, having $N_r$ (e.g., 1000) elements 18 disposed along the in-plane (x,y) direction, and $N_z$ (e.g., 16) elements 18 disposed along the z axis. The x-ray beam emanates from the x-ray source 13 and fans out as it passes through the patient 15 and intercepts the detection array 16. Each acquired view is a $N_r$ by $N_z$ array of attenuation measurements as seen when the gantry is oriented in one of its positions during the scan. The object of the present invention is to reconstruct a set of 2D image slices from the 3D array of acquired data produced by the x-ray cone beam during the scan.

Because the cone beam diverges as it passes through the patient 15, the reconstruction of the parallel image slices is not possible with a straight forward fan beam filtering and backprojecting process. The present invention enables an accurate reconstruction of the image slices from this acquired cone beam data. In addition, the present invention enables the accurate reconstruction of image slices even when the path of the x-ray source 13 is less than a complete circle or is a spiral path or is a circle and a straight line path, or is two concentric circles.

Figure 12:
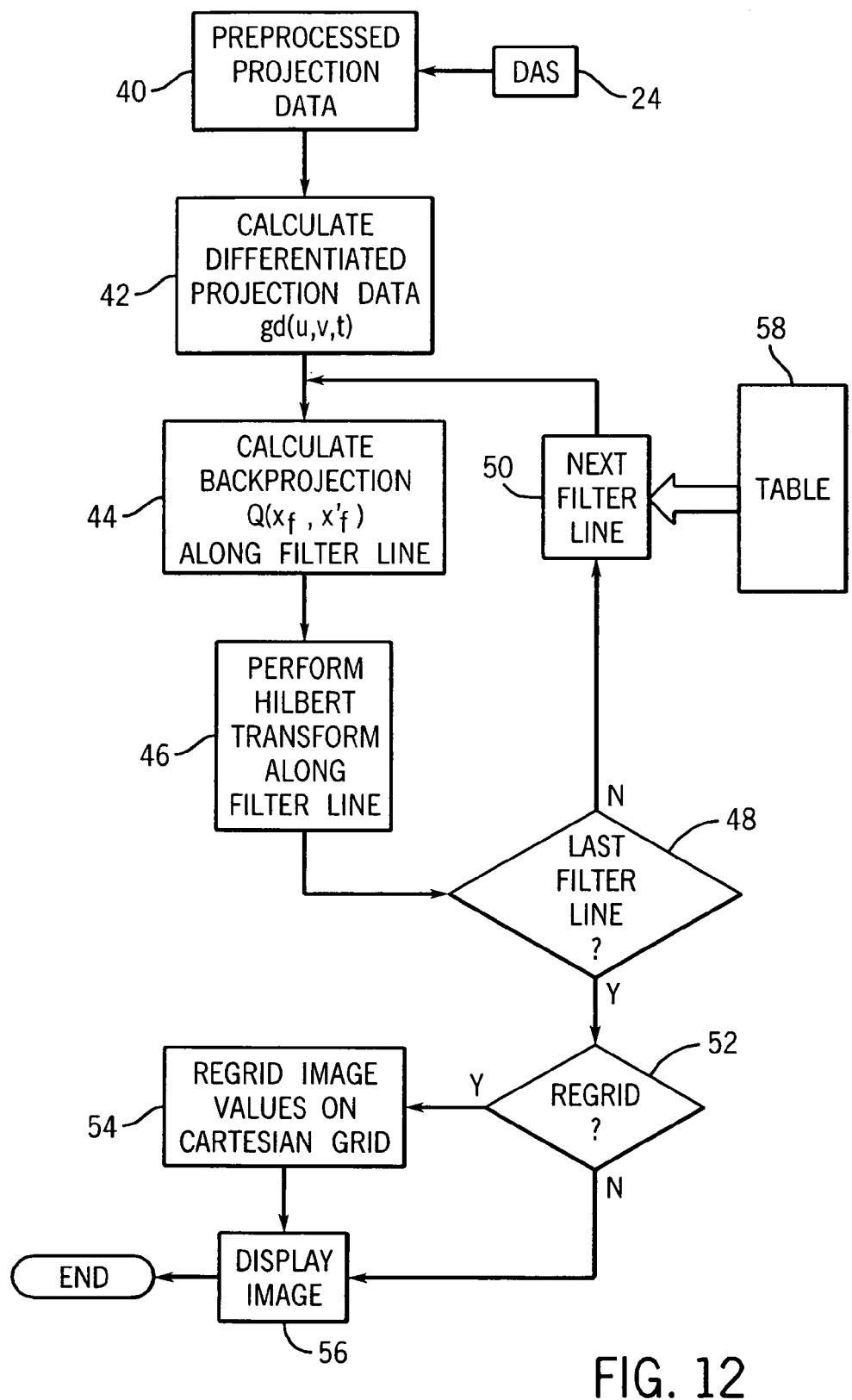
FIG. 12 is a flow chart of the steps performed by the imaging system of FIGS. 6 and 7 to practice a preferred embodiment of the present invention.

This reconstruction method is implemented in the image reconstructor 25. Referring particularly to FIG. 12, the cone beam projection data is received from the DAS 24 as a two-dimensional array of values which are preprocessed in the standard manner at process block 40. Such preprocessing includes correcting for known errors and offsets and calculating the minus log of the data to convert it to x-ray attenuation values.

As indicated at process block 42, the next step is to differentiate the preprocessed attenuation profiles $g_m$ (u,v,t) by calculating the weighted derivatives. With the flat detector shown in FIG. 5 this is done according to the above Eq. 4.57, whereas Eq. 4.58 is employed when the attenuation data is acquired with a curved detector.

A loop is then entered in which each image pixel value $f(x_f)$ is calculated by a filtered backprojection process. As described above, this is done one filter line at a time, and the choice of the number and direction of filter lines to be used in the image reconstruction will depend on the particular scan performed and image prescribed. More specifically, the weighted backprojection $Q(x_f, x'_f)$ at each image pixel along a filtering line is calculated as indicated at process block 42. This is done according to Eq. (2.26) using projection views that were acquired over a segment of the source trajectory indicated by Eq. (??). The backprojected values are weighted by the product of weighting factor $\omega_2(\vec{x}'_f, t)$ and the inverse of the distance between the backprojection image point and the x-ray source point $(1/|\vec{x}'_f - \vec{y}(t)|)$ as indicated in Eq. (2.26).

As indicated at process block 46, the backprojected values along the filter line are filtered using a finite range Hilbert transform as set forth above in Eq. (4.55). This produces the final image values at points along the filter line and a test is then made at decision block 48 to determine if additional image points need to be calculated. If so, the next filter line is selected as indicated at process block 50 and the process repeats. As will be explained in more detail below with the specific case studies, the nature of this test and the manner in which the next filter line is selected will depend on the particular strategy used to reconstruct an image from the acquired data set. Suffice to say that the process repeats until the image values at locations throughout image space are calculated with sufficient density that an image of prescribed resolution can be produced.

Depending on the particular reconstruction strategy chosen, the calculated image values may or may not lie on a Cartesian grid. If not, as determined at decision block 52, a regridding process is used at process block 54 to calculate the image values at points on a Cartesian grid. This is a well-known step used in medical imaging and it may be an interpolation of the calculated image values or a convolution based distribution. The resulting Cartesian image may then be displayed and stored in Hounsfield units in the usual fashion as indicated at process block 56.

Referring still to FIG. 12, in one preferred embodiment of the present invention the image reconstruction process is directed by a table 58 which stores a set of filter line locations and associated weighting factors $\omega_2(\vec{x}, t)$. These have been predetermined for the prescribed scan as a list of filter lines and weighting functions $\omega_2(\vec{x}, t)$ which are properly supported by the acquired data set. The process described above repeats for each of the filter lines listed in table 58 until all of the listed filter lines have been used. This is determined at decision block 48. The direction as well as the location will be different for each filter line in the general case.

There is a special case in which a series of filter lines can be defined which reconstruct the image as image points on a Cartesian grid. That is, the filter lines are all in the same direction, but are spaced apart from each other the same distance. This special case is for a fan beam acquisition as described above in case 1. In this embodiment the parallel filter lines are reconstructed one at a time until all of the lines needed to cover the prescribed image region of interest as determined at decision block 48.

Figure 13:
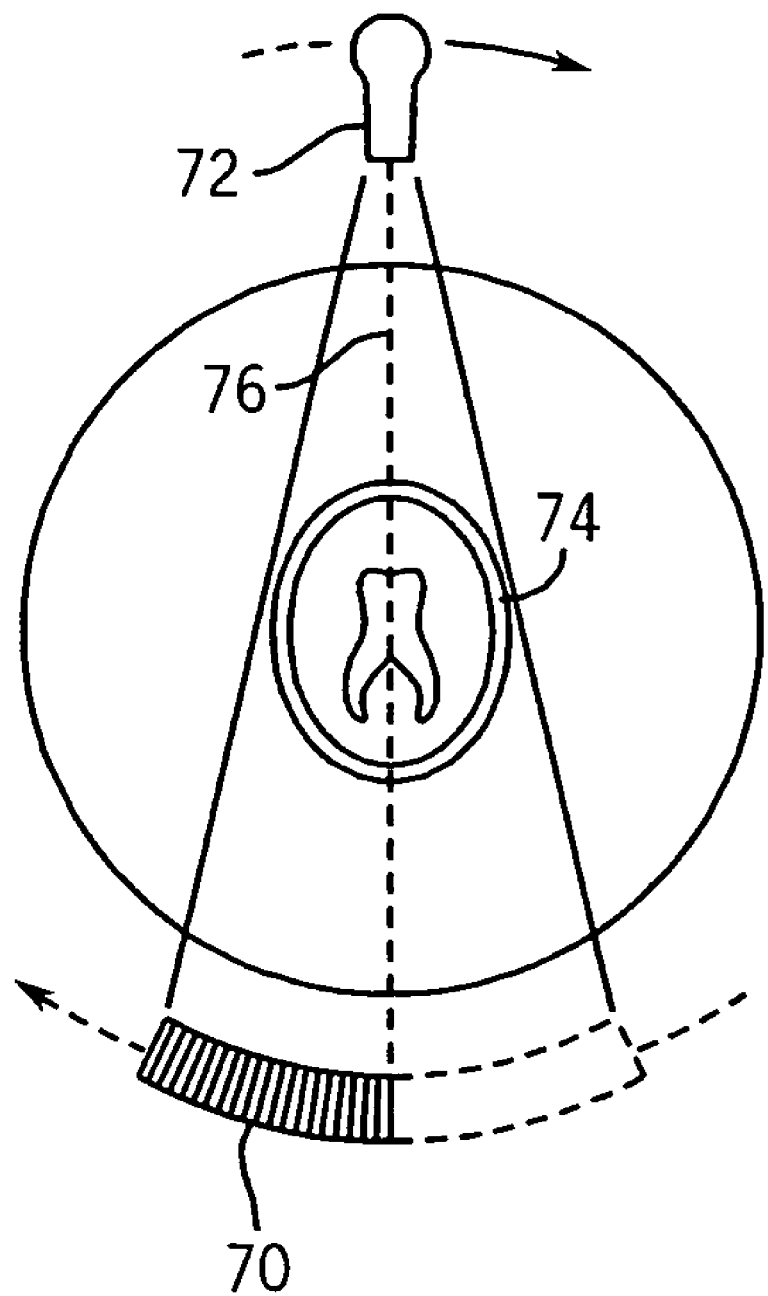
FIG. 13 is a pictorial representation of an asymmetric detector used in an alternative embodiment of the invention.

Another preferred embodiment of the invention employs the present invention to reconstruct an image acquired with a fan beam configuration with data truncation at every acquired projection view. This continuous view truncation (CVT) application is illustrated in FIG. 13 where an asymmetric detector 70 covers only one-half of the field of view of the fan beam produced by x-ray source 72. The detector 70 is asymmetric in that the detector elements are located to one side of the iso-ray 76. As the x-ray source 72 and detector 70 revolve around the subject 74 in a circular path, only one-half the projection data is acquired at each view angle.

Using the above-described image reconstruction method it proved possible to accurately reconstruct an image of the entire subject 74 if the source 72 and detector 70 performed a complete 2π revolution around the subject 74. A series of radial filter lines were used that passed from one boundary of the field of view and through the isocenter to the opposite boundary. In computing the backprojection image of differentiated projection data, the derivatives were calculated by a three point formula. A Hann window was used to used to suppress the high frequency fluctuations in the reconstructed images. The constant C in Eq. 4.55 was determined by using Eq. 4.56. A bilinear interpolation scheme was used to find the projection values for a given filtering line. Namely, when the intersection of the filtering line and the circular source trajectory is not right on a discrete focal spot, we need to draw two parallel lines from two nearby focal spots and use the projection values of these two parallel lines to interpolate the projection value at the filtering line. However, these two parallel lines may not hit on the detector cells. In order to obtain the projection values at these two parallel lines, linear interpolation may also have to be introduced in the detector plane. Thus, we may have interpolation in view angles and in detector cells.

It has also been discovered that images of selected subregions of the subject 74 can be accurately reconstructed from data sets acquired with CVT even when the scan covers less than a complete 2π revolution. In this case the filter lines are not radial, but a series of parallel filter lines through the subregion at an angle that is supported by projection views in the acquired data set. For example, if the subregion of interest is the heart which is a small part of the entire field of view, the scan can be shortened to less than the short-scan requirement of 180° plus fan angle.

By imposing a factorization property on the weighting function $\omega(\vec{x}, \vec{k}; t)$ of a cone-beam inversion formula and its fan-beam counterpart, an image reconstruction method can be defined as an integral of a product of two functions: $K(\vec{x}, \vec{x}')$ and $Q(\vec{x}, \vec{x}')$. The function $Q(\vec{x}, \vec{x}')$ is the weighted backprojection of differentiated projection data acquired over a suitable range of view angles. The function $K(\vec{x}, \vec{x}')$ is the Fourier transform of one of the two weighting factors $\omega_1(\vec{x}, \vec{k})$. By choosing the second weighting factor $\omega_2(\vec{x}, \vec{k})$ to be piecewise constant, practical reconstruction methods result in which a filtering kernel is reduced to a Hilbert kernel or a linear combination of Hilbert kernels applied along different filtering lines. In order to calculate the backprojection image $Q(\vec{x}_f, \vec{x}'_f)$, only one x-ray projection from one view angle is required. Therefore, the detector size is not required to be large enough to cover the whole image object or the whole transverse cross section and both transverse data truncation and longitudinal data truncations are allowed using this reconstruction method. A detector that is not large enough to cover the transverse cross section of the image object or the longitudinal cross section may be dynamically or adaptively translated or moved during data acquisition to acquire attenuated projection data profiles for a complete backprojection image $Q(\vec{x}_f, \vec{x}'_f)$.

A number of implementation variations are possible with the present method. The differentiated projection data $g_d(u, v; t)$ or $g_d(\gamma, a; t)$ may be approximately calculated using the numerical difference between two nearby data points. The differentiated projection data $g_d(u, v; t)$ or $g_d(\gamma, a; t)$ may also be approximately calculated using fast Fourier transforms (FFT) in the Fourier domain. The Hilbert transform may be calculated in the real space domain using a shifted and addition method, or the Finite Hilbert transform may be calculated in the Fourier domain using FFT.

This image reconstruction method may be utilized in other tomographic imaging modalities such as MRI, PET, SPECT, thermalacoustic CT (TCT), and photoacoustic CT (PCT). The detectors may be flat panel CT detectors, curved CT detectors, gamma cameras (SPECT) or a transducer (TCT and PCT), or read-out coils (MRI). The constant C in the finite range Hilbert transform may also be determined using the physical information that the image values should be zero outside the image support. Namely, when an image point is selected outside the image support, the constant C is given by the negative value of the integral in the square bracket of Eq. (4.55). Also, the integral limit in the finite Hilbert transform Equation (4.55) may be selected to be symmetric (A=−B).

It should be apparent that the selection of filtering line location and orientation is flexible. For a given targeted reconstruction region of interest or volume, one may select different filtering lines to fill that entire image volume or region. The filtering line direction may be selected along a pi-line, a generalized pi-line, or an arbitrary line that connects the image points and a preselected source position (open chord). For any image point inside a volume or region of interest, there should exist at least one straight line that passes through the image point and intersects the source trajectory at two points in its scan trajectory. Otherwise, the method is not limited to particular scan trajectories or detector geometries.

The invention claimed is:
1. A method for producing an image with a tomographic imaging system, the steps comprising:
  a) performing a scan in which a plurality of beams are produced by a source and corresponding projection views of a subject are acquired at different view angles;
  b) differentiating the acquired projection views;
  c) producing image values by backprojecting a differentiated projection view along a filter line that passes through image space and weighting the backprojected value by the product of a weighting factor and the inverse of the distance between the projection view source and the image value location;

d) filtering the image values along the filter line; and e) repeating steps c) and d) to produce additional filtered image values along different filter lines throughout a region of interest in image space.

2. The method as recited in claim 1 which step d) employs a Hilbert transformation over a finite range.

3. The method as recited in claim 1 in which the filter lines are substantially parallel to each other.

4. The method as recited in claim 3 in which the filtered image values along the filter lines are substantially uniformly distributed throughout the region of interest.

5. The method as recited in claim 1 which includes:

f) regridding the filtered image values such that they are substantially uniformly distributed throughout the region of interest.

6. The method as recited in claim 1 in which the filter lines are radially directed and pass through the center of image space at different angles.

7. The method as recited in claim 6 which includes:

f) regridding the filtered image values such that they lie on the Cartesian grid in image space.

8. The method as recited in claim 1 in which step a) is performed by detecting a divergent beam.

9. The method as recited in claim 8 in which the divergent beam is a fan beam.

10. The method as recited in claim 8 in which the divergent beam is a cone beam.

11. The method as recited in clam 8 in which the divergent beam is detected symmetrically about an iso-ray.

12. The method as recited in claim 8 in which the divergent beam is detected asymmetrically about an iso-ray.

13. The method as recited in claim 8 in which the divergent beam is produced by an x-ray source moving in a path around the subject.

14. A method for producing an image with a tomographic imaging system, the steps comprising:

a) performing a scan in which a plurality of divergent beam projection views of a subject are acquired at different view angles;

b) differentiating the acquired projection views; and c) producing an image from the acquired projection views which is an integral of a product of two functions, K and Q, where the function Q is a weighted backprojection operation on the differentiated projection view data, where the function K is a Fourier transform of a first weighting factor $\omega_1$, that is one of two weighting factors $\omega_1$ and $\omega_2$ that result from factorizing a weighting function $\omega$.

15. The method as recited in claim 14 in which the weighting function $\omega_2$ is piecewise constant.

* * * * *